(12) United States Patent
Ruha

(10) Patent No.: US 11,576,589 B2
(45) Date of Patent: Feb. 14, 2023

(54) APPARATUS, SYSTEM AND METHOD OF RESPIRATORY INDUCTANCE PLETHYSMOGRAPHY WITH MEASUREMENT BANDS

(71) Applicant: BITTIUM BIOSIGNALS OY, Kuopio (FI)

(72) Inventor: Antti Ruha, Kuopio (FI)

(73) Assignee: BITTIUM BIOSIGNALS OY, Kuopio (FI)

(*) Notice: Subject to any disclaimer, the term of this patent is extended or adjusted under 35 U.S.C. 154(b) by 310 days.

(21) Appl. No.: 16/883,060

(22) Filed: May 26, 2020

(65) Prior Publication Data

US 2020/0383604 A1 Dec. 10, 2020

(30) Foreign Application Priority Data

Jun. 7, 2019 (EP) .................................... 19178960

(51) Int. Cl.
| | |
|---|---|
| *A61B 5/08* | (2006.01) |
| *G01F 17/00* | (2006.01) |
| *A61B 5/00* | (2006.01) |
| *A61B 5/0295* | (2006.01) |
| *A61B 5/091* | (2006.01) |

(52) U.S. Cl.
CPC ............ *A61B 5/0809* (2013.01); *A61B 5/002* (2013.01); *A61B 5/0295* (2013.01); *A61B 5/091* (2013.01); *A61B 5/6823* (2013.01); *A61B 5/6831* (2013.01)

(58) Field of Classification Search
CPC ....... A61B 5/05; A61B 5/0806; A61B 5/0816; A61B 5/091; A61B 5/1135; A61B 5/6802; A61B 5/7225; A61B 5/7278; A61M 2230/40
See application file for complete search history.

(56) References Cited

U.S. PATENT DOCUMENTS

| | | | |
|---|---|---|---|
| 2002/0123701 A1* | 9/2002 | Eriksen | .................. A61B 5/091 600/595 |
| 2019/0000376 A1* | 1/2019 | Rahman | ............... A61M 16/024 |

OTHER PUBLICATIONS

Extended Search Report for EP19178960.1, dated Nov. 22, 2019, 8 pages.

* cited by examiner

*Primary Examiner* — Lawrence S Galka
(74) *Attorney, Agent, or Firm* — Nixon & Vanherhye PC

(57) ABSTRACT

An apparatus comprising at least two RIP measurement bands further comprises an electric power source arrangement, which excites simultaneously the at least two measurement bands with electric currents of different pseudo random variations, for making respiratory signals output by the at least two measurement bands unique. The apparatus also comprises a wireless transmitter arrangement, which transmits wirelessly respiratory information based on the respiratory signals output by the at least two measurement bands.

10 Claims, 3 Drawing Sheets

APPARATUS, SYSTEM AND METHOD OF RESPIRATORY INDUCTANCE PLETHYSMOGRAPHY WITH MEASUREMENT BANDS

This application claims priority to EP 19178960.1 filed 7 Jun. 2019, the entire contents of which is hereby incorporated by reference.

FIELD

The invention relates to an apparatus, system and method of respiratory inductance plethysmography with measurement bands.

BACKGROUND

Breathing of a person or more generally a mammal may be measured using a pneumotachometer, which is cumbersome, or using two belts of a respiratory inductance plethysmography, which is typically considered less cumbersome. Each of the two elastic belts comprise an electrically conducting wire, and as the belts encircle the body, an electrically conducting wire of each of the belts forms a loop or a coil. In a typical measurement arrangement, one of the belts is located at the chest and another is located at the abdomen. To measure inductances of the coils of the belts, an exciting operational power in a form of alternating electric current is fed to the coils. An inductance of the coil of the belt at the chest depends on a cross sectional area of the chest, and an inductance of the coil of the belt at the abdomen depends on a cross sectional area of the abdomen. Because breathing varies the cross sectional areas and thus the inductances, breathing may be measured on the basis of a variation of the inductances.

However, magnetic coupling between the coils of the different belts i.e. mutual inductance disturbs the inductive respiratory measurement.

There have been attempts to have the exciting electric current frequencies of the chest and abdominal belts separated in order to decrease the magnetic coupling. The respiratory inductance plethysmography belt impedance has parasitic components and exiting and measuring at different frequencies might result in measurement error due to unknown parasitic components.

Instead of the frequency separation of the exciting electric current, also temporal separation of the exciting electric current has been proposed. Then an inductance of one belt is measured at a moment when no current is fed to another belt, and vice versa. However, this requires accurate time base between the sensors in order to avoid shift as a function of time. This is a viable solution when time base can be guaranteed to be accurate, for example with two or more RIP belts with wired connections to a hub. However with two or more wireless belts the drifting of oscillation frequencies will result in a loss of time sync and loss of measurement accuracy.

Additionally, the wiring between the belts and data analyser is disturbing to the user, particularly during a long measurement.

Hence, the problem of mutual inductance still limits respiratory inductance plethysmography, and there is a need to improve the respiratory measurement particularly when using respiratory inductance plethysmography belts.

BRIEF DESCRIPTION

The present invention seeks to provide an improvement in the measurements.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of a respiratory inductance plethysmography system, which comprises at least two measurement bands round the body of a user;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may also contain features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus and/or system may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
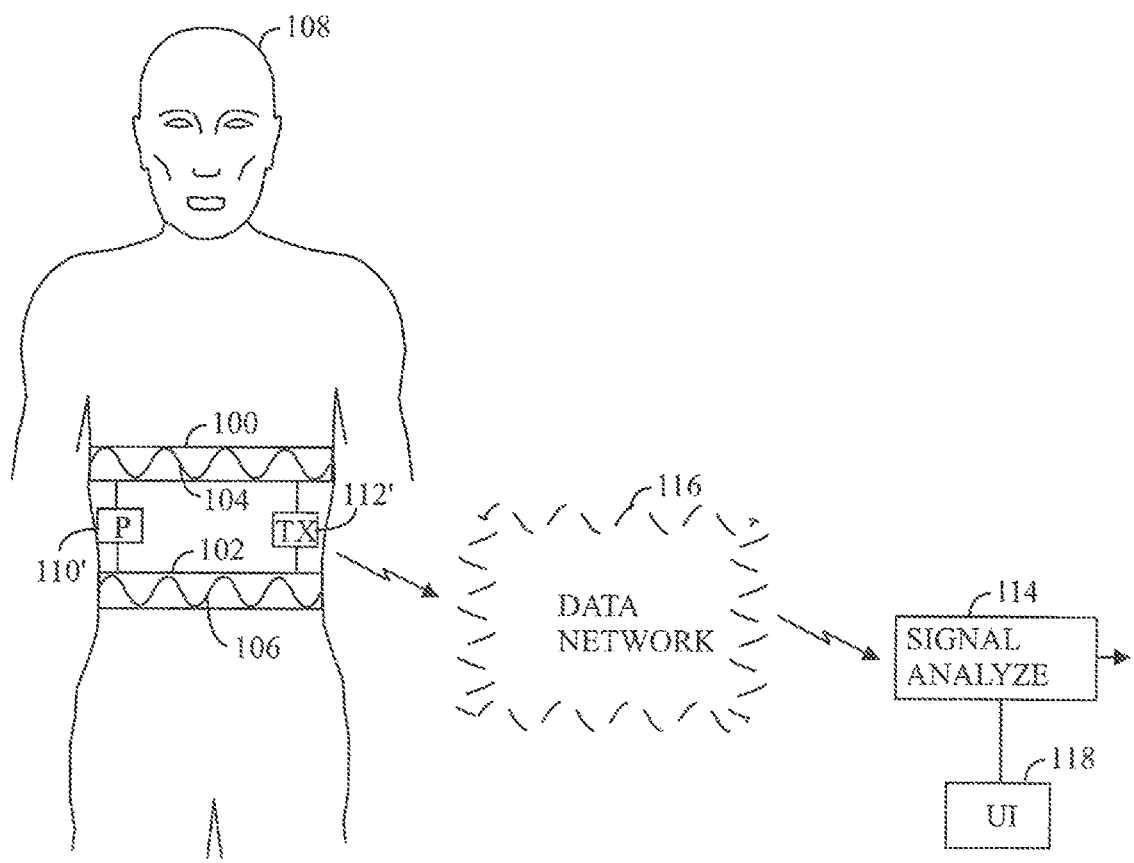

FIG. 1 illustrates an example of an apparatus comprising at least two measurement bands 100, 102 of respiratory inductance plethysmography. A corresponding system comprises also a signal analyzer 114. A user 108 wears at least two elastic measurement bands 100, 102, each of which has a wire as a coil (shown as a sinusoidal curve within each of the bands). One of the bands 100 may be located at the thorax and another of the bands 102 may be located at the abdomen, for example. In any case, the measurement bands 100, 102 are located at different sections of the torso of the user 108. The bands 100, 102, which may be belts or the like, may be elastic in order to stretch and bend. Each of the two bands 100, 102 comprise an electrically conducting wire 104, 106. The electrically conducting wires 104, 106, which may be bent in shapes of sinusoidal, triangular (triangles one after another) or any zigzag waveforms in order to allow the bands to stretch, form loops or coils round the body of a user 108. This measurement arrangement allows the change of the cross sectional area due to inhaling and exhaling.

The apparatus also comprises an electric power source arrangement 110, which may be an electric current sink or source. The power source arrangement excites each of the at least two measurement bands 100, 102 of the respiratory inductance plethysmography by feeding them alternating electric current as a pseudo random operational power signal. The alternating electric current includes successive electric current pulses. The electric current pulses of a first measurement band of the measurement bands 100, 102 may have a pseudo random sequence. The electric current pulses of a second or any other of the measurement bands 100, 102 then have a pseudo random sequence, which is different from that of the first measurement band.

Alternatively or additionally, the electric current pulses of a first measurement band of the measurement bands 100, 102 may have a pseudo random amplitude distribution. The electric current pulses of a second or any other of the measurement bands 100, 102 then have a pseudo random amplitude distribution, which is different from that of the first measurement band.

The electric current fed to the measurement bands 100, 102 for creating the pseudo random variation to their output is coded using pseudo random codes. Examples of the pseudo random codes are Maximum Length sequences, Walsh Hadamard sequences, Gold codes, and Kasami codes. A pseudo random code may be generated with a pseudo random sequence generator 206', 206", which may be application. The application, in turn, may be realized as a hardware, i.e. as an electric circuit, or as software, i.e. as a computer program. The initial seed for the pseudo random code generation of each of the measurement bands 100, 102 may be based on an individual identifier. In this manner, the pseudo random code is different for different measurement bands 100, 102, and may be utilized distinguishing the respiratory signals from the measurement bands 100, 102. The initial seed may be based on a unique serial number of a measurement band 100, 102, for example.

In an embodiment, the apparatus may comprise a common electric power source to all the measurement bands 100, 102.

Figure 2:
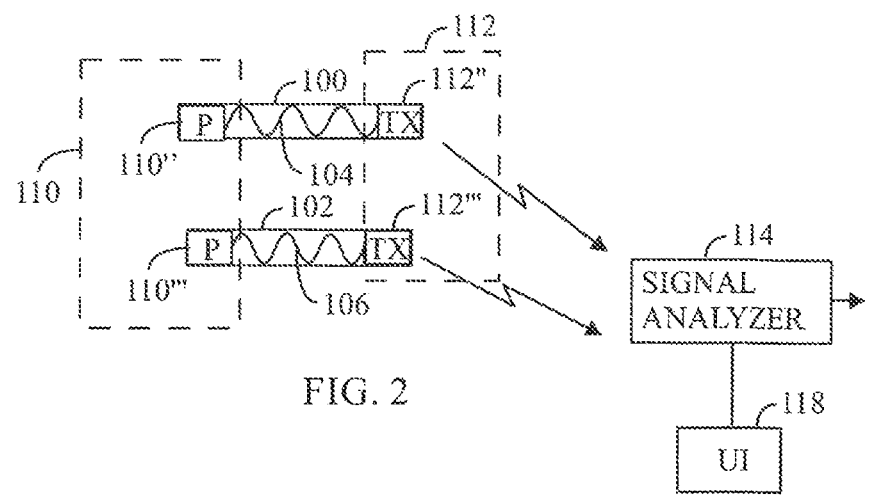
FIG. 2 illustrates an example of measurement bands of the respiratory inductance plethysmography system which have separate power sources and separate transmitters.

In an embodiment, the apparatus may comprise a common electric power source for a plurality of the measurement bands 100, 102 while at least two of the measurement bands 100, 102 has a separate electric power source. In an embodiment, which is illustrated in FIG. 2, each of the measurement bands 100, 102 may comprise an electric power source 110", 110''' of its own such that none of the electric power sources 110", 110''' is common to any of the measurement bands 100, 102.

The electric power source arrangement 110, which may comprise a common electric power source 110' or separate electric power sources 110", 110''', thus excites simultaneously each of the at least two measurement bands 100, 102 of respiratory inductance plethysmography with different pseudo random variations of the operational power signals. The pseudo random variation may be based on a pseudo random sequence of electric current pulses and/or a pseudo random amplitude distribution of the electric current pulses. The pseudo random variations of the operational power signals cause different pseudo random variations of magnetic fields through cross sections of the body at the locations of the measurement bands 100, 102. Because breathing varies the cross sectional areas and thus the magnetic fields of the coils of the stretching measurement bands 100, 102 round the body, breathing may be measured on the basis of a variation of the inductances of the coils. The variations of the inductances of the different measurement bands 100, 102 are unique because of the different pseudo random operational power signals fed to the measurement bands 100, 102. Hence, respiratory signals, which are based on inductance and which are output by the at least two measurement bands 100, 102 of respiratory inductance plethysmography, are unique. Because the respiratory signals are unique they can be distinguished and separate from each other.

The measurement may be based on a mutual inductance M and coefficient of coupling k between the coils of the measurement bands 100, 102. The coupling may be determined in the following manner: $k*M=k*\sqrt{L1*L2}$, where L1 is an inductance of the measurement band 100 and L2 is an inductance of the measurement band 102. The inductances L1 and L2 have a response to a variation of a cross section of the body of the user 108 and the coefficient of coupling k may be used to estimate a distance between the bands 100, 102. In this manner, it is possible to estimate a breathing volume more effectively.

The apparatus comprises also a wireless transmitter arrangement 112, which transmits wirelessly respiratory information based on the respiratory signals output by the at least two measurement bands 100, 102 of respiratory inductance plethysmography.

In an embodiment, the transmitter arrangement 112 may utilize Bluetooth™, WLAN (Wireless Local Area Network), WiFi or the like. In an embodiment, the wireless transmission from the transmitter arrangement 112 to the signal analyzer 114 may be performed through a data network 116. In an embodiment, the data network 116 may be a local network, the Internet or any combination thereof. In an embodiment, the transmission of the transmitter arrangement 112 or the wireless transmission may be based on a cellular network of a radio system such as 3G, LTE network (Long Term Evolution) of 4G or 5G, for example.

In an embodiment, the transmitter arrangement 112 may transmit the respiratory signals directly to a signal analyzer 114, which may reside in the environment. Then no information processing of the respiratory signals is performed but, for example, filtering may be performed. The signal analyzer 114 has a user interface 118 which may comprise a keyboard, a screen and/or a touch screen for presenting measurement results. The keyboard and/or the touch screen may be used to input data. The respiratory data analyzing unit 114 may form respiratory parameter data. Additionally or alternatively, the respiratory data analyzing unit 114 may present the respiratory parameter data with a user interface 118 of the data analyzing unit 114.

In an embodiment, the apparatus may comprise a common wireless transmitter arrangement 112 to all the measurement bands 100, 102. In an embodiment, the apparatus may comprise a common wireless transmitter arrangement 112' to a plurality of the measurement bands 100, 102. In an embodiment, the transmitter arrangement 112 may comprise separate transmitters 112", 112''' different measurement bands 100, 102.

Figure 4:
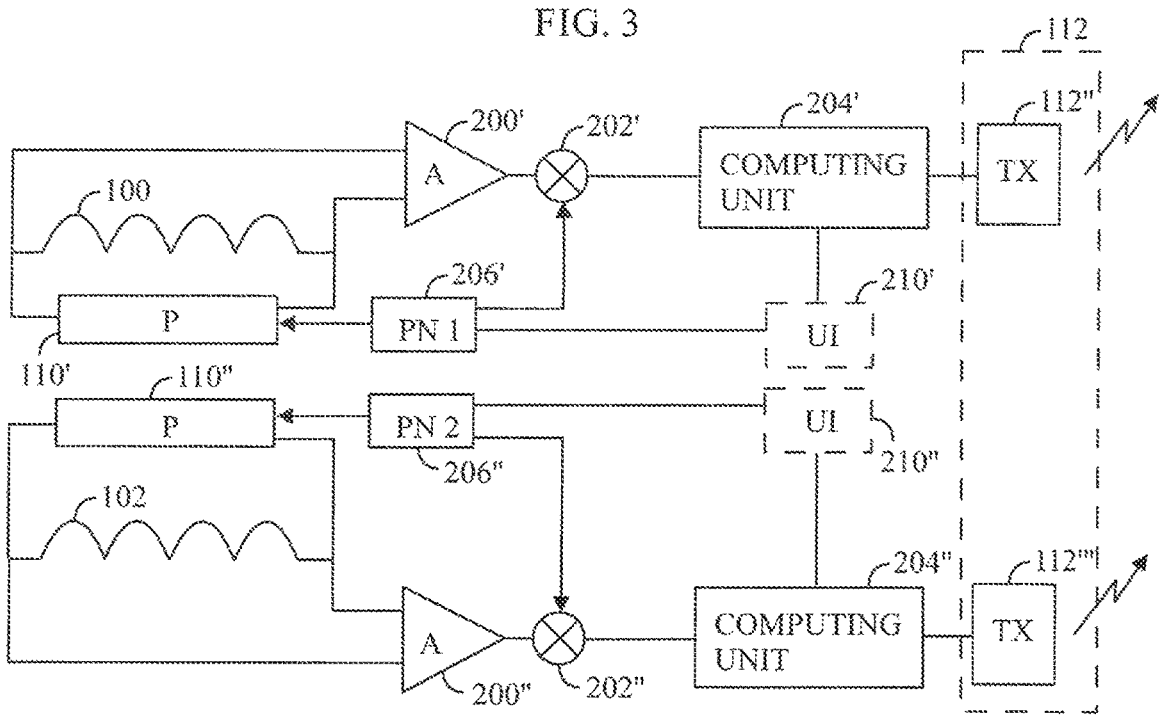
FIG. 4 illustrates an example where separate measurement bands have individual computing units and transmitters.

In an embodiment, which is illustrated in FIG. 2 or 4, each of the measurement bands 100, 102 may comprise a wireless transmitter 112", 112''' of its own. In an embodiment, at least two of the measurement bands 100, 102 may comprise a common wireless transmitter but separate electric power sources 110", 110'''. In an embodiment, at least two of the measurement bands 100, 102 may comprise a common electric power source 110' but separate wireless transmitters 112", 112'''. The respiratory data analyzing unit 114 may comprise a wireless receiver that is a counterpart of the transmitter arrangement 112 or the separate transmitters 112", 112''', the receiver being suitable for receiving a transmission of the common transmitter 112' or the separate transmitters 112", 112'''.

Figure 3:
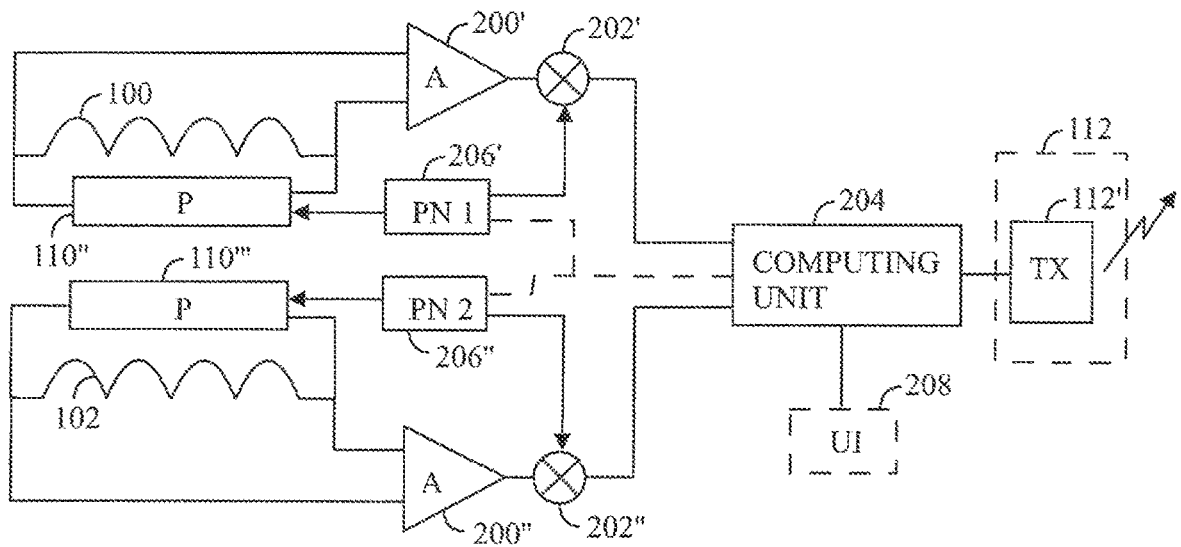
FIG. 3 illustrates an example where a computing unit and a transmitter arrangement is common to two or more measurement bands.

In an embodiment an example of which is illustrated in FIG. 3, the power source arrangement 110 comprises a separate power source 110", 110''' for each of the measurement bands 100, 102. The pseudo random sequence generator 206' feeds a pseudo random sequence to a electric power source 110" of the measurement band 100, and controlled by the pseudo random sequence, the electric power source 110" feeds a pseudo random operational power signal to the one of the measurement bands 100. In a corresponding manner, a pseudo random sequence generator 206" feeds a pseudo random sequence to the electric power source 110''', and controlled by the pseudo random sequence, the electric power source 110''' provides the one of the measurement bands 102 with a pseudo random operational power signal.

In the respiratory inductance plethysmography, the electric power source 110" applies electric current through the loop of wire of one of the measurement bands 100, and the electric current causes a magnetic field perpendicular to a direction of the electric current and a normal to an area surrounded by the loop. A change in the area enclosed by the loop, in turn, generates an electric current that has a determined relation to the change of the area. Then a voltage signal may be detected over the coil of the measurement band 100 by a sensing circuit, which typically comprises an amplifier (see pre-amplifier 200' in FIGS. 3 and 4) and an analog-digital converter.

Correspondingly, the electric power source 110''' applies electric current through the loop of wire of one of the measurement bands 102. Then a voltage signal may be detected over the coil of the measurement band 102 by a sensing circuit, which typically comprises an amplifier (see pre-amplifier 200" in FIGS. 3 and 4) and an analog-digital converter.

The voltage signal, which is encoded with a pseudo random sequence, may be decoded using the same pseudo random sequence as done in the encoding phase. Hence, the pseudo random sequence generators 106', 106" also provide decoders 202', 202" with the pseudo random sequences. Then, the apparatus may decode, using the decoders 202', 202", the respiratory signals of the at least two measurement bands 100, 102. The decoders 202', 202" may be applications which, in turn, may be implemented as hardware, i.e. as electric circuits, or as software, i.e. as computer programs. The decoders 202', 202" may dismantle the pseudo random variations of the operation power signals from the respiratory signals, and uncover information about the breathing of the user 108.

The decoders 202', 202" may multiply the respiratory signals from the measurement bands 100, 102 with corresponding pseudo random codes. Before decoding the respiratory signals from the measurement bands 100, 102 may be amplified and/or filtered with pre-amplifying circuits 200', 200". Additionally, the decoded respiratory signal may be filtered in order to remove disturbances from the changes in inductance. In an embodiment, the filtering may be performed as low-pass filtering. In an embodiment, the filtering may be performed as band-pass filtering.

In an embodiment, the apparatus may perform an association between a respiratory signal and a measurement band that output said respiratory signal. The apparatus may associate an identification information related to a measurement band 100, 102 and a corresponding decoded respiratory signal with each other for making respiratory signals from the at least two measurement bands 100, 102 distinguishable from each other. The association may be performed by a computing unit arrangement which may comprise a common computing unit 204 or separate computing units 204', 204". A comparison between the decoded respiratory signals may be performed for analysing breathing, because the common computing unit 204 or the signal analyzer 114 distinguishes, on the basis of the identification information, which decoded respiratory signal belongs to which measurement band.

The identification of a first measurement band 100 can be associated with a respiratory signal of the first measurement band 100, and an identification of a second measurement band 102 can be associated with a respiratory signal of the second measurement band 102. In general, an identification of a n:th measurement band can be associated with a respiratory signal of the n:th measurement band, where n is a whole number larger than 1. Then the transmitter arrangement 112 may transmit as the respiratory information, which includes both the respiratory signals with their identification information.

The identification information may comprise a unique serial sequence of symbols of a measurement band 100, 102, for example. The serial sequence of symbols may comprise at least one number and/or one writing symbol, for example. The serial sequence of symbols may comprise alphanumeric symbols, for example. The serial sequence of symbols may comprise a serial number of a measurement band 100, 102.

The apparatus may perform the association between each of the measurement bands 100, 102 and each of the respiratory signals such that any respiratory signal is associated with a unique measurement band 100, 102 or vice versa.

Additionally, the respiratory signals may be associated with timing information about recording moments of the respiratory signals. The association with the timing information may be performed by the common computing unit 204 or separate computing units 204', 204". A recording moment of a respiratory signal may refer to recording of the respiratory signal as a function of time, where there is a deterministic dependence between values of the respiratory signal and moments of time. Then the respiratory signals or the respiratory information of different measurement bands 100, 102, which is recorded at the same moment, can be compared for analysing breathing.

In an embodiment, the at least two measurement bands 100, 102 may have a common user interface 208 or the measurement bands 100, 102 may have separate user interfaces 210', 210" of their own. The user interfaces 208, 210', 210" may comprise a keyboard, a screen and/or a touch screen. The user 108 or some other person may input data to the common computing unit 204 or the separate computing units 204', 204" such as the identification information and/or the initial seed for the pseudo random sequences.

In an embodiment an example of which is illustrated in FIG. 3, the apparatus may comprise the common computing unit 204, which forms respiratory parameter data on the basis of the respiratory signals. The common computing unit 204 may form respiratory parameter data repeatedly from the respiratory signals. The common computing unit 204 then feeds the respiratory parameter data to the transmitter arrangement 112, which in this example is the common transmitter 112', which wirelessly transmits the respiratory parameter data as the respiratory information for the signal analyzer 114.

FIG. 4 illustrates an example where each of the measurement bands 100, 102 has a computing unit 204', 204" of its own. FIG. 4 also illustrates an example where each of the measurement bands 100, 102 has a transmitter 112", 112''' of its own.

In an embodiment, the apparatus does not form the respiratory parameter data in the common computing unit 204 and the separate computing units 204', 204". Then the signal analyzer 114 may form the respiratory parameter data from the respiratory information sent to it.

The respiratory parameter data may, for example, comprise information related to values of volume of the cross section of the body of the user 108 at the locations, where the measurement bands 100, 102 are, as a function of time. The respiratory parameter data may, for example, comprise information related to changes of the values of the volume of the cross section of the body of the user 108 at the locations, where the measurement bands 100, 102 are, as a function of time. When the respiratory data of the different measurement bands 100, 102 is compared by the signal analyzer 114 or by the common computing unit 204 to the measurement bands 100, 102, information about the breathing of the user 108 may be formed.

The respiratory parameter data corresponds to the respiratory data of the prior art except that the mutual inductance between the measurement bands 100, 102 have been reduced or eliminated based on the pseudo random variations of the electric current fed to the measurement bands 100, 102. The improved elimination of the mutual inductance may increase accuracy and reliability of the respiratory parameter data and final information about the breathing of the user 108.

A system of the respiratory inductance plethysmography comprises the at least two measurement bands 100, 102, the electric power source arrangement 110 with one electric power source 110' or a plurality of electric power sources 110", 110''', the decoder 202, 202', 202", the transmitter arrangement 112 with one transmitter 112' or a plurality of transmitters 112", 112''' and the respiratory data analyzing unit 114.

In an embodiment, the electric power source arrangement 110 may excite a first band 100 using a first pseudo random signal PN1, and a first decoder 202' may decode the respiratory signal of the first band 100 using the first pseudo random signal PN1. The electric power source arrangement 110 may excite the second band 102 using a second pseudo random signal PN2, and a second decoder 202" may decode the respiratory signal of the second band 102 using the second pseudo random signal PN2. The computing unit 204 may then form respiratory parameter data on the basis of the decoded respiratory signals.

In an embodiment, the electric power source arrangement 110 may excite a first band 100 using a first pseudo random signal PN1, and a second decoder 202" may decode the respiratory signal of the second band 102 using the first pseudo random signal PN1. The electric power source arrangement 110 may excite the second band 102 using a second pseudo random signal PN2, and a first decoder 202' may decode the respiratory signal of the first band 100 using the second pseudo random signal PN2. The computing unit 204 may then form respiratory parameter data on the basis of the decoded respiratory signals.

Figure 5:
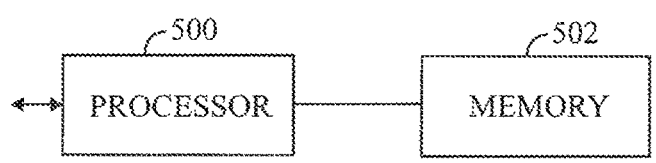
FIG. 5 illustrates an example where a signal analyzer or a computing unit has at least one processor and at least one memory.

FIG. 5 illustrates an example of the signal analyzer 114 and the computing units 204, 204', 204", which may comprise one or more processors 500 and one or more memories 502. A suitable computer program stored in the one or more memories 502 may be used to perform the analysis of the respiratory signals in the common computing unit 204 or in the signal analyzer 114. The common computing unit 204 may control an operation of the at least two measurement bands 100, 102. Any of the separate computing units 204', 204", each of which belongs to only one of the measurement bands 100, 102 while different measurement bands 100, 102 have different computing units 204', 204", may control only the measurement band 100, 102 a part of which it is.

For example, the measurement bands 100, 102 may provide respiratory signals, an analysis of which in the signal analyzer 114 or the common computing unit 204 results in a fact that the chest and the thoracic diaphragm move at substantially out of phase. In another example, the measurement bands 100, 102 may provide respiratory signals, an analysis of which in the signal analyzer 114 or the common computing unit 204 results in a fact that the chest and the thoracic diaphragm move substantially simultaneously. This kind of information may be important to a nursing personnel and/or a doctor of the user 108.

Because both the input and output of each of the measurement bands 100, 102 are encoded and decoded with pseudo random sequences, the measurement bands 100, 102 may be excited and read continuously and simultaneously. The pseudo random sequences correlate poorly, and thus they provide a clear separation between the operations of the measurement bands 100, 102. In addition, there is no need to have time synchronization between the excitation and reading of the measurement bands 100, 102.

Additional benefit of the encoding and decoding with the pseudo random sequences is an added tolerance against external noise (such as mains coupling) coupling to the measurement bands 100, 102, as it is modulated to other frequency band in the decoding process and may be attenuated by the low pass filtering.

Figure 6:
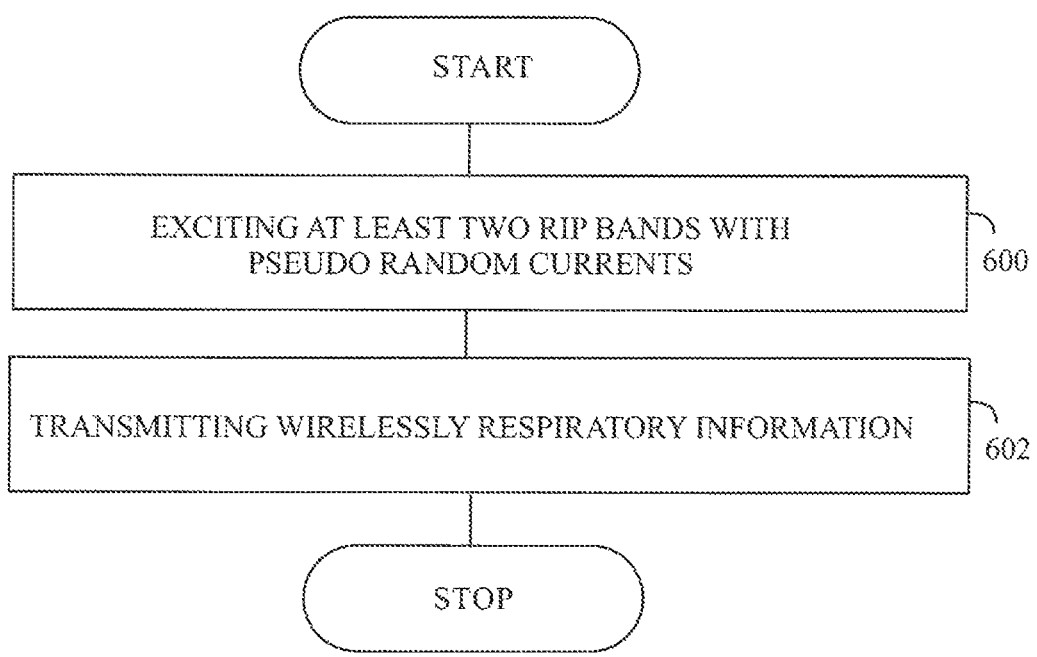
FIG. 6 illustrates an example of a flow chart of a respiratory inductance plethysmography method.

FIG. 6 is a flow chart of the respiratory inductance plethysmography method. In step 600, the at least two measurement bands 100, 102 are excited simultaneously with electric currents of different pseudo random variations by an electric power source arrangement 110, for making respiratory signals output by the at least two measurement bands 100, 102 unique. In step 602, respiratory information based on the respiratory signals output by the at least two measurement bands 100, 102 are transmitted wirelessly by a wireless transmitter arrangement 112.

Figure 7:
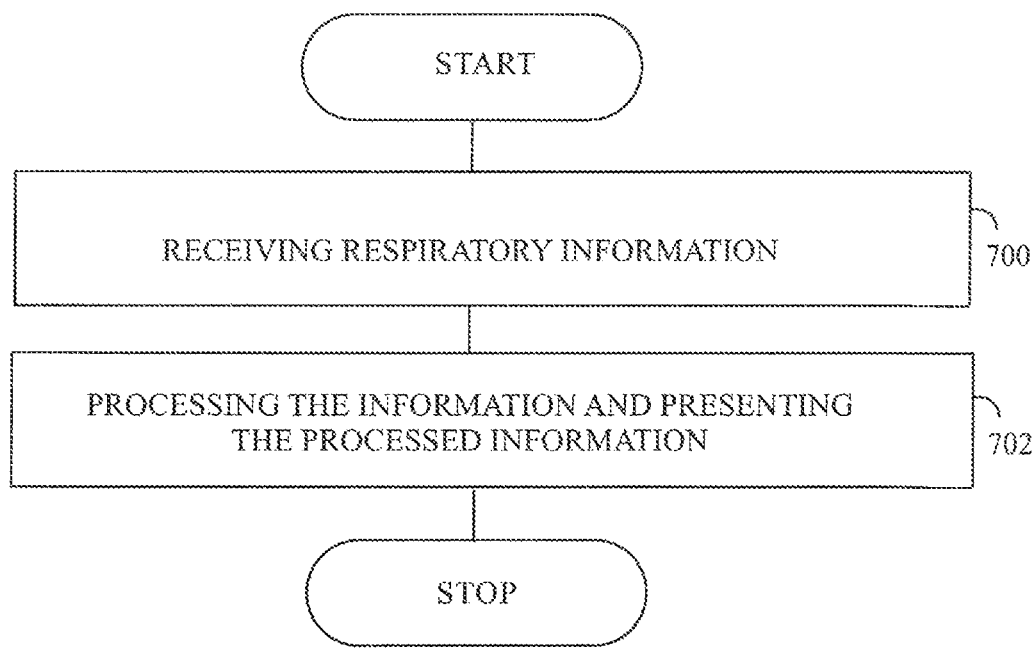
FIG. 7 illustrates an example of a flow chart of a data processing method.

FIG. 7 is a flow chart of the data processing method in either the common computing unit 204 or the signal analyser 114. In step 700, respiratory information is received. In step 702, the respiratory information is processed. The processing may include respiratory parameter data formation and/or presentation.

The formation of the respiratory parameter may be performed by a suitable computer program. The computer program may be placed on a computer program distribution means for the distribution thereof. The computer program distribution means is readable by the common computing unit 204 and/or the signal analyser 114, and it encodes the computer program commands, carries out the required steps.

The computer program may be distributed using a distribution medium which may be any medium readable by the controller. The medium may be a program storage medium, a memory, a software distribution package, or a compressed software package. In some cases, the distribution may be performed using at least one of the following: a near field communication signal, a short distance signal, and a telecommunications signal.

It will be obvious to a person skilled in the art that, as technology advances, the inventive concept can be implemented in various ways. The invention and its embodiments are not limited to the example embodiments described above but may vary within the scope of the claims.

What is claimed is:

1. An apparatus of respiratory inductance plethysmography comprising:
    at least two measurement bands of respiratory inductance plethysmography;
    an electric power source configured to excite simultaneously the at least two measurement bands with electric currents of different pseudo random variations, to make respiratory signals output by the at least two measurement bands unique, the electric power source being configured to excite simultaneously the at least two measurement bands with electric currents that have different pseudo random amplitude distributions; and
    a wireless transmitter configured to transmit wirelessly respiratory information based on the respiratory signals output by the at least two measurement bands.

2. The apparatus of claim 1, wherein the electric power source is configured to excite simultaneously the at least two measurement bands with successive pulses of electric currents that have different pseudo random sequences.

3. The apparatus of claim 1, wherein the electric power source is configured to excite simultaneously the at least two measurement bands with electric currents that have different pseudo random amplitude distributions.

4. The apparatus of claim 1, wherein the apparatus is configured to:
    decode the respiratory signals of the at least two measurement bands; and
    perform an association of an identification information about a measurement band and a respiratory signal, which is decoded and related to said measurement band, with each other for making respiratory signals from the at least two measurement bands distinguishable; and
    wherein the transmitter is configured to transmit the respiratory signals with the identification information as the respiratory information.

5. The apparatus of claim 1, wherein the apparatus comprises a computing unit common to the at least two measurement bands and configured to form respiratory parameter data based on the respiratory signals; and
    the transmitter is configured to transmit the respiratory parameter data as the respiratory information.

6. The apparatus of claim 5, wherein the common computing unit comprises:
    one or more processors; and
    one or more memories including computer program code;
    the one or more memories and the computer program code configured to, with the one or more processors, cause the common computing unit at least to perform at least one of the following: form respiratory parameter data and present the respiratory parameter data with a user interface of the common computing unit.

7. A system comprising:
    at least two measurement bands of respiratory inductance plethysmography;
    an electric power source configured to excite simultaneously the at least two measurement bands with electric currents of different pseudo random variations, to make respiratory signals output by the at least two measurement bands unique;
    decoders configured to decode the respiratory signals of the at least two measurement bands;
    a computing unit configured to perform an association between a respiratory signal and an identification information about a measurement band, which output said respiratory signal, with each other;
    a wireless transmitter configured to transmit wirelessly respiratory information about the respiratory signals with the identification information; and
    a respiratory data analyzer configured to receive the respiratory information transmitted wirelessly for data processing.

8. The system of claim 7, wherein the respiratory data analyzer comprises:
    one or more processors; and
    one or more memories including computer program code;
    the one or more memories and the computer program code configured to, with the one or more processors, cause the respiratory data analyzer at least to perform at least one of the following: form respiratory parameter data and present the respiratory parameter data with a user interface of the data analyzer.

9. A respiratory inductance plethysmography method, the method comprising:
    exciting simultaneously, by an electric power source, at least two measurement bands with electric currents of different pseudo random variations, for making respiratory signals output by the at least two measurement bands unique; and
    transmitting wirelessly, by a wireless transmitter, respiratory information based on the respiratory signals output by the at least two measurement bands.

10. The method of claim 9, further comprising receiving, by a respiratory data analyzer, the information about the respiratory signals; and
    processing the information, and presenting the processed information with a user interface of the data analyzer.

* * * * *